US010702138B2

(12) United States Patent
Cantrell

(10) Patent No.: US 10,702,138 B2
(45) Date of Patent: Jul. 7, 2020

(54) ILLUMINATED LARYNGOSCOPE

(71) Applicant: Elroy T. Cantrell, Lynchburg, VA (US)

(72) Inventor: Elroy T. Cantrell, Lynchburg, VA (US)

(*) Notice: Subject to any disclaimer, the term of this patent is extended or adjusted under 35 U.S.C. 154(b) by 349 days.

(21) Appl. No.: 15/287,034

(22) Filed: Oct. 6, 2016

(65) Prior Publication Data

US 2018/0098692 A1   Apr. 12, 2018

(51) Int. Cl.
*A61B 1/267* (2006.01)
*A61B 1/06* (2006.01)
*A61B 1/04* (2006.01)

(52) U.S. Cl.
CPC ........... *A61B 1/267* (2013.01); *A61B 1/04* (2013.01); *A61B 1/0669* (2013.01)

(58) Field of Classification Search
CPC ................................................ A61B 1/267
See application file for complete search history.

(56) References Cited

U.S. PATENT DOCUMENTS

| 4,320,745 A * | 3/1982 | Bhitiyakul | A61B 1/07 600/138 |
| 4,425,909 A * | 1/1984 | Rieser | A61B 1/267 600/197 |
| 5,178,132 A * | 1/1993 | Mahefky | A61B 1/267 600/194 |
| 6,719,688 B2 * | 4/2004 | Pecherer | A61B 1/267 600/188 |
| 2005/0240081 A1 * | 10/2005 | Eliachar | A61B 1/267 600/199 |
| 2007/0156022 A1 * | 7/2007 | Patel | A61B 1/267 600/199 |

* cited by examiner

*Primary Examiner* — Andrew Yang
(74) *Attorney, Agent, or Firm* — William G. Sykes

(57) ABSTRACT

A dual blade laryngoscope having a folding handle and a manually installable lighting cartridge. The laryngoscope includes two spaced apart parallel blades and a wall spanning both. A slot is formed at one end of the parallel blades for receiving the lighting cartridge. A translucent or transparent lens covers a visualization channel defined between the parallel blades. The folding handle includes an axle to enable pivoting between a deployed position and a stowed position, and a projection which activates the lighting cartridge. The lighting cartridge and the transparent lens are removable. Each of the parallel blades has a curved portion at forward ends thereof to facilitate managing soft tissue and directional control of an endotracheal tube during insertion in a patient. A tooth guard pad of compliant rubber-like material may be permanently affixed to the underside of lower blade.

15 Claims, 4 Drawing Sheets

ILLUMINATED LARYNGOSCOPE

FIELD OF THE DISCLOSURE

The present disclosure relates to laryngoscopes, and more particularly, to a folding, dual blade laryngoscope having a modular lighting cartridge.

BACKGROUND

Insertion of an endotracheal tube through a laryngoscope into a patient is frequently difficult to visualize due to presence of soft tissues which may slump to obstruct direct view. This threatens successful intubation, for example.

Laryngoscopes having onboard illumination are known. However, an effective, compact, uncomplicated replaceable lighting arrangement for laryngoscopes has remained elusive.

In addition to mere presence of illumination in a laryngoscope, to be effective illumination requires an unobstructed channel or path for projecting light along the line of sight of the operator.

There remains a need for improved lighting and visualization in laryngoscopes, these not being satisfactorily met by present art.

SUMMARY

The disclosed concepts address the above stated situation by providing a laryngoscope including a relatively large and unobstructed pathway for projected light and sighting by a human operator. A C-shaped channel provides such a pathway. One end of the pathway may bear a clear transparent or translucent lens, a camera, or both. Lighting may be provided by an easily inserted lighting cartridge containing a battery, a light emitting diode light source, and a switch.

The novel laryngoscope may include a folding handle. Moving the handle out of the folded or stowed position not only locks the handle into a deployed position wherein the handle is generally perpendicular to the light pathway and blades, but also operates the switch of the lighting cartridge. Hence opening the handle into the deployed position switches on the light, and returning the handle to the stowed position extinguishes the light, thereby conserving battery power.

It is an object to provide improved elements and arrangements thereof by apparatus for the purposes described which is inexpensive, dependable, and fully effective in accomplishing its intended purposes.

These and other objects will become readily apparent upon further review of the following specification and drawings.

BRIEF DESCRIPTION OF THE DRAWINGS

Various objects, features, and attendant advantages of the disclosed concepts will become more fully appreciated as the same becomes better understood when considered in conjunction with the accompanying drawings, in which like reference characters designate the same or similar parts throughout the several views, and wherein.

DETAILED DESCRIPTION

Figure 1:
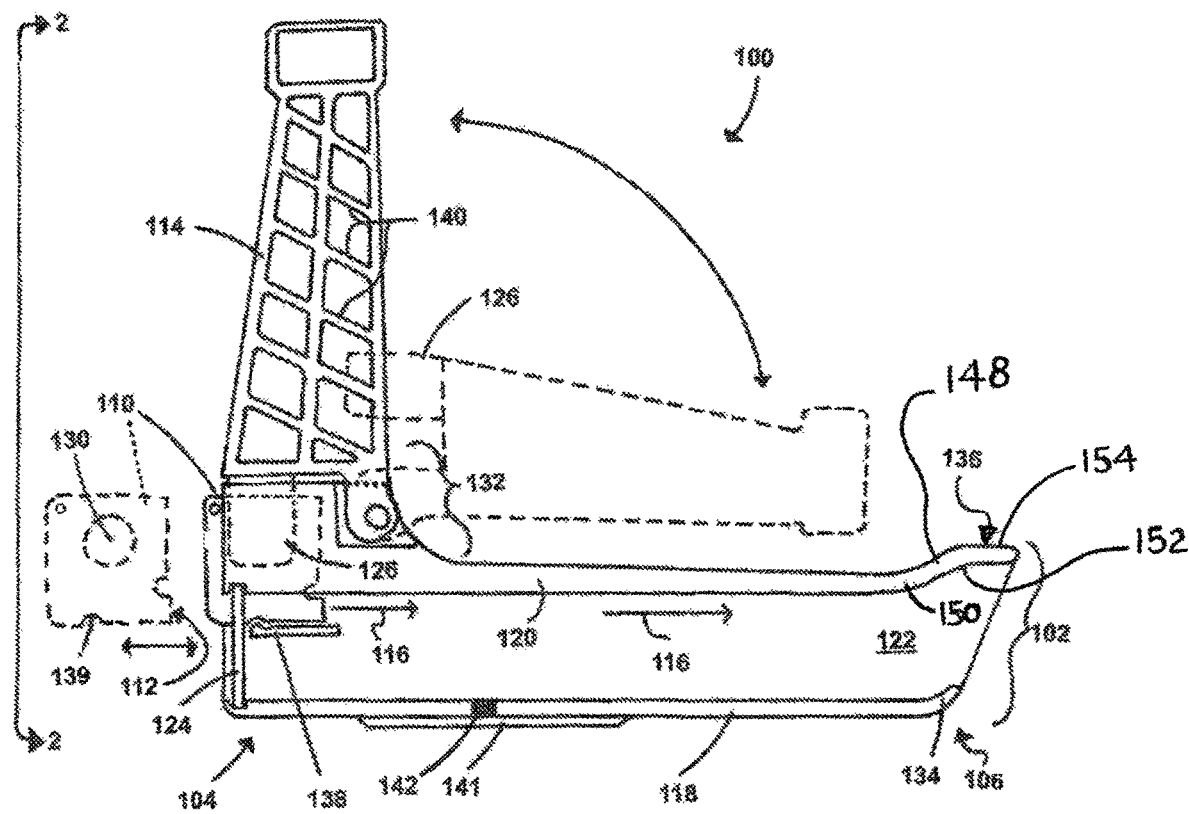
FIG. 1 is a side elevational view of a laryngoscope according to at least one aspect of the disclosure.
Figure 2:
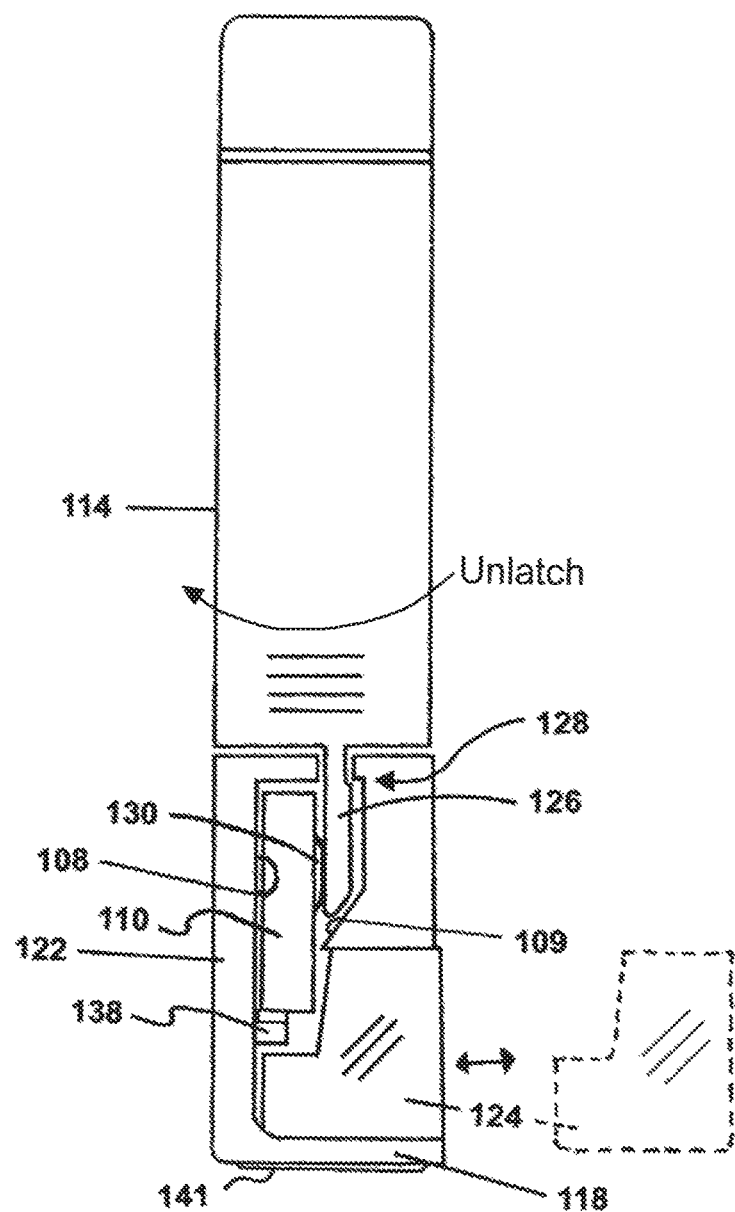
FIG. 2 is a proximal end elevational view of FIG. 1, taken along line 2-2.

Referring first to FIG. 1, according to at least one aspect of the disclosure, there is shown a laryngoscope 100 comprising a blade structure 102 generating a bounded pathway 116 for projected light and visualization. Blade structure 102 comprises a proximal end 104, an opposed distal end 106, and a slot 108 (see FIG. 2) for receiving a lighting cartridge 110 proximate proximal end 104. Lighting cartridge 110 is configured and dimensioned to be received in slot 108. Lighting cartridge 110 comprises a light source 112 facing distal end 106 of blade structure 102 when lighting cartridge 110 is inserted into slot 108. Laryngoscope 100 includes a handle 114 at a non-parallel angle to blade structure 102. Laryngoscope 100 has a generally inverted pistol grip configuration in the deployed condition. Pathway 116 for light is preferably below upper blade 120, or alternatively stated, along the underside of upper blade 120.

Blade structure 102 may comprise a first blade 118 straight along at least seventy-five percent of its length, a generally parallel second blade 120 spaced apart from first blade 118 in overlying relation to first blade 118 and straight along at least eighty percent of its length, and a lateral wall 122 spanning first blade 118 and generally parallel to second blade 120. This configuration leaves bounded pathway 116 unobstructed by bodily tissues (not shown). As seen in FIG. 1, first blade 118 is in a lower position relative to second blade 120.

In laryngoscope 100, lighting cartridge 110 may protrude from the blade assembly when fully seated in slot 108, whereby lighting cartridge 110 may be grasped and withdrawn from blade assembly 102 by finger contact. Lighting cartridge 110 may be left in slot 108 during storage and removed therefrom for service, such as for battery renewal. Alternatively, lighting cartridge 110 may be replaced as a unit. Lighting cartridge 110 may be secured in place by a latch finger 138. Latch finger 138 may include a projection configured to occupy a recess 139 in lighting cartridge 110, and is deflected to release lighting cartridge 110 for removal. Lateral maneuvering of lighting cartridge 110 (in a direction parallel to bounded pathway 116) by manual pressure disengages latch finger 138 from recess 139.

Laryngoscope 100 may comprise an optional transparent lens 124 coupled to blade structure 102 perpendicular to slot 108. Transparent lens 124 covers bounded pathway 116 at proximal end 104, serving as a spatter shield preventing discharge of bodily fluids from a patient onto operator. Transparent lens 124 may be slidably removable from and installable to blade structure 102 for ready installation, and so as not to require small parts such as fasteners.

Figure 5:
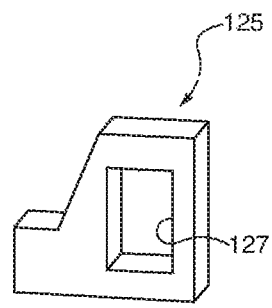
FIG. 5 is a perspective detail view of an alternative to an element shown at the lower right of FIG. 2.

Transparent lens 124 may also be replaced by a properly adapted camera. To this end, and referring also to FIG. 5, laryngoscope 100 may further comprise a camera mount 125 coupled to blade structure 102 perpendicular to slot 108. Camera mount 125 may be slidably removable from and installable to blade structure 102 the same way as transparent lens 124, for example by sliding interfit retained by friction. Camera mount 125 may be structurally similar to transparent lens 124 at the outer periphery of camera mount, but may differ from transparent lens 124 in having an opening 127 for receiving a camera (not shown). The camera may be removably retained within camera mount 125 by friction fit.

Slot 108 extends along a direction parallel to bounded pathway 116, whereby lighting cartridge 110 is inserted in a direction from proximal end 104 of the blade structure towards distal end 106 of blade structure 102. This arrangement enables intuitive installation of lighting cartridge 110.

Handle 114 may be pivotally coupled to blade structure 102 and may be movable between the deployed position generally perpendicular to blade structure 102 to a stowed position non-perpendicular to blade structure 102. Handle 114 may thus be folded for compactness of laryngoscope 100. The deployed position is shown in solid lines, and the stowed position is indicated in broken lines in FIG. 1.

Figure 4:
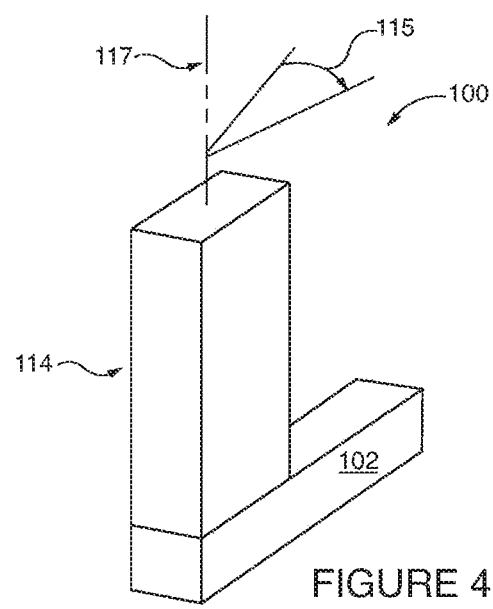
FIG. 4 is a diagrammatic perspective view of FIG. 1, with some structural details omitted.

Optionally, one of blade structure 102 and handle 114 comprises a projection 126, and the other of blade structure 102 and handle 114 comprises an aperture 128 (see FIG. 2) configured and dimensioned to receive projection 126 in close cooperation and to retain projection 126 by latch and friction fit. Engagement locks handle 114 in the deployed position, yet allows handle 114 to be easily unlatched and returned to the stowed position when desired by twisting handle 114 clockwise (called out as "unlatch" in FIG. 2, and further illustrated in FIG. 4) and folding handle down. In FIG. 4, handle 114 is rotated slightly, directionally shown as arrow 115 about handle longitudinal axis 117. In the stowed position, handle 114 may be parallel to and abutting blade structure 102. This achieves significant compactness when laryngoscope 100 is not being used.

Lighting cartridge 110 may comprise a switch including a switch operator 130 externally accessible from lighting cartridge 110. Handle 114 comprising projection 126 may engage switch operator 130 when handle 114 is moved to the deployed position. Upon deployment the slope of the right sidewall 109 of slot 108 causes the distal end of projection 126 to press laterally against the dome of switch operator 130 causing the switch to be activated. Therefore, lighting cartridge 110 automatically projects light when handle 114 is in the deployed position, and automatically conserves battery power when handle 114 is in the stowed position.

Switch operator 130 may be configured as a moveable dome or covered by a flexible skin. Projection 126 deforms the flexible dome when engaging switch operator 130. Switch operator 130 is therefore protected from contamination such as from bodily fluids, while still being readily operated by contact with projection 126.

Blade structure 102 and handle 114 may be configured to form an anterior continuous curve from blade structure 102 to handle 114 when handle 114 is in the deployed position. The curve is indicated in FIG. 1 as a region 132. The continuous curve avoids configurations which could catch or pinch the fingers when using laryngoscope 100.

First blade 118 may comprise an upwardly directed bend 134 at the distal end of blade structure 102. Bend 134 is upwardly directed when held in a normal orientation such as that depicted in FIG. 1. It should be noted at this point that orientational terms such as upwardly refer to the subject drawing as viewed by an observer. The drawing figures depict their subject matter in orientations of normal use, which could obviously change with changes in body posture of the user. Therefore, orientational terms must be understood to provide semantic basis for purposes of description only, and do not imply that their subject matter can be used only in one position.

Upper blade 120 may comprise a multicurved scoop 136 at distal end 106 of blade structure 102. Bend 134 and multicurved scoop 136 may be used to maneuver anatomical features when finding optimal positioning of laryngoscope 100 in a patient see FIG. 3). The epiglottis 144 is lifted upward, revealing glottis 145, behind which lies vocal cords 146. The bend 134 can deflect the tip of an endotracheal tube upward into glottis 145 and decrease risk of entry into the esophagus.

As seen in FIG. 1, multicurved scoop 136 comprises a first leg 148 at distal end 106 of the second blade 120. First leg 148 projects at a first bend 150 from second blade 120 at a non-parallel angle thereto in a direction away from lens 124. A second bend 152 occurs at an end of first leg 148. A second leg 154 projects from second bend 152 at a second non-parallel angle in the direction away from lens 124.

First blade 118 comprises upwardly directed bend 134 at distal end 106 of blade structure 102, and multicurved scoop 136 may project a different length from proximal end 104 of blade structure 102 than does upwardly directed bend 134 of first blade 118. For example, FIG. 1 illustrates bend 136 extending further than bend 134. This configuration has proved effective when displacing or maneuvering collapsed anatomical structures of the throat.

Handle 114 may be unlatched from the deployed position by slightly twisting handle 114. This releases a latch at 128 such that handle 114 is unlatched. Handle 114 is readily returned to the original folded position by light manual pressure.

Handle 114 may include exposed walls 140 or other texturing to improve grip by the user. Walls 140 form separated compartments, while stabilizing handle 114. Deep compartments conserve the amount of constituent material used and limit final weight of laryngoscope 100.

A cushion pad 141 of compliant material such as neoprene may be permanently affixed to underside of lower blade 118, so as to reduce risk of injury to teeth due to manual pressure when inserting and maneuvering laryngoscope 100.

Laryngoscope 100 may be fabricated from a mildly resilient synthetic resin, so that projection 126 and latch finger 138 can deflect under manual pressure or force, but will remain in their respective positions absent manual pressure or force.

Figure 3:
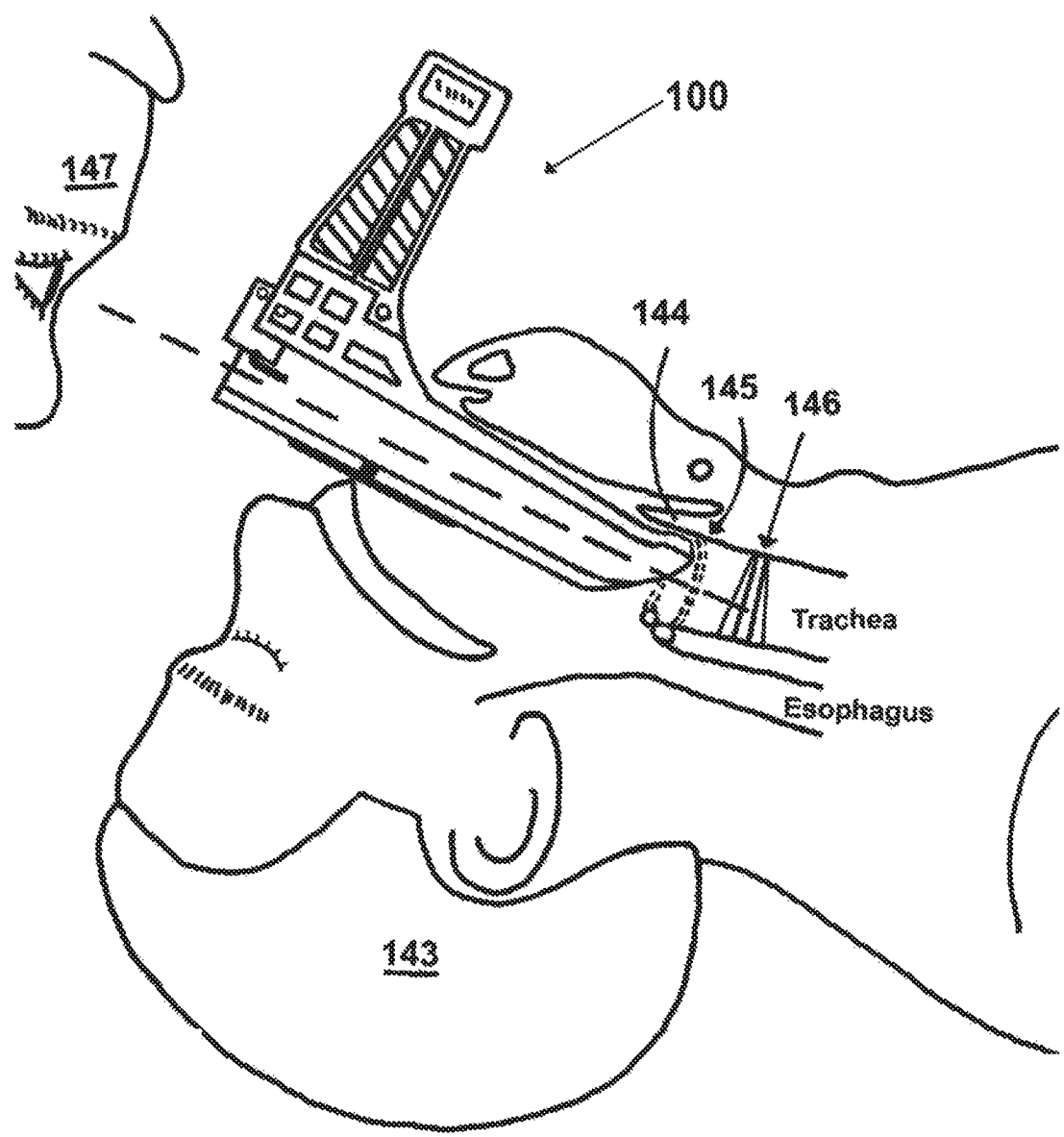
FIG. 3 is a diagrammatic environmental view showing use of the laryngoscope of FIG. 1.

FIG. 3 shows laryngoscope 100 inserted into the throat of a patient 143, as would occur for example in a medical emergency situation. Laryngoscope 100 is inserted into the right side of opened mouth and the tip slid along the palate during insertion until the tip is positioned so that the glottis and vocal cords are visualized. Medical or emergency personnel 147 is shown visualizing appropriate placement of laryngoscope within patient 143.

As seen in FIGS. 1 and 3, laryngoscope 100 further comprises a depth marker 142 visible from the exterior of laryngoscope 100 when laryngoscope 100 is inserted into patient 143. Depth marker 142 is placed so that operator 147 of laryngoscope 100 can insert first and second blades 118, 120 quickly, until depth marker 142 is at approximately the level of the right lip margin. Final positioning of laryngoscope 100 is performed under direct visualization along bounded pathway 116. Depth marker 142 may comprise a color different from that of blade structure 102, or may otherwise be visually discernible.

Unless otherwise indicated, the terms "first", "second", etc., are used herein merely as labels, and are not intended to impose ordinal, positional, or hierarchical requirements on the times to which these terms refer. Moreover, reference to, e.g., "second" item does not either require or preclude the existence of, e.g., a "first" or lower-numbered item, and/or, e.g., a "third" or higher-numbered item.

It should be understood that the various examples of the apparatus(es) disclosed herein may include any of the components, features, and functionalities of any of the other examples of the apparatus(es) disclosed herein in any feasible combination, and all of such possibilities are intended to be within the spirit and scope of the present disclosure. Many modifications of examples set forth herein will come to mind to one skilled in the art to which the present disclosure pertains having the benefit of the teachings presented in the foregoing descriptions and the associated drawings.

Therefore, it is to be understood that the present disclosure is not to be limited to the specific examples presented and that modifications and other examples are intended to be included within the scope of the appended claims. Moreover, although the foregoing description and the associated drawings describe examples of the present disclosure in the context of certain illustrative combinations of elements and/or functions, it should be appreciated that different combinations of elements and/or functions may be provided by alternative implementations without departing from the scope of the appended claims.

I claim:

1. A laryngoscope comprising:
a blade structure generating a bounded pathway for projected light and visualization, the blade structure comprising a proximal end and an opposed distal end, wherein the blade structure comprises a first blade straight along at least seventy-five percent of its length, a generally parallel second blade spaced apart from the straight first blade in overlying relation to the first blade and straight along at least eighty percent of its length, and a straight lateral wall spanning the straight first blade and the generally parallel second blade, wherein the first blade comprises an upwardly directed bend projecting toward the generally parallel second blade at the distal end of the blade structure, and the generally parallel second blade comprises a multicurved scoop at the distal end of the blade structure, wherein the multicurved scoop comprises a first leg at the distal end of the second blade, the first leg projecting at a first bend from the second blade at a non-parallel angle thereto in a direction away from a lens, a second bend at an end of the first leg, and a second leg projecting from the second bend at a second non-parallel angle in the direction away from the lens, and the multicurved scoop projects further from the proximal end than does the upwardly directed bend of the straight first blade and is configured to leave the bounded pathway for projected light and visualization unobstructed from the proximal end and the opposed distal end;
a light source at the proximal end of the blade structure, facing the distal end of the blade structure; and
a handle at a non-parallel angle to the blade structure, the handle proximate the proximal end of the blade structure.

2. The laryngoscope of claim 1 wherein
the blade structure comprises a slot for receiving a lighting cartridge proximate the proximal end;
the light source comprises a lighting cartridge configured and dimensioned to be received in the slot, wherein the light source projects light toward the distal end of the blade structure when the lighting cartridge is inserted into the slot; and
the lighting cartridge protrudes from the blade assembly when fully seated in the slot, whereby the lighting cartridge may be grasped and withdrawn from the blade assembly by finger contact.

3. The laryngoscope of claim 1, further comprising a translucent lens coupled to the blade structure perpendicular to the slot, the translucent lens covering the bounded pathway.

4. The laryngoscope of claim 3, wherein the translucent lens is removable from and installable to the blade structure.

5. The laryngoscope of claim 1, further comprising a camera mount coupled to the blade structure perpendicular to the slot.

6. The laryngoscope of claim 1, wherein the camera mount is removable from and installable to the blade structure.

7. The laryngoscope of claim 2, wherein the slot extends along a direction parallel to the bounded pathway, whereby the cartridge is inserted in a direction from the proximal end of the blade structure towards the distal end of the blade structure.

8. The laryngoscope of claim 1, wherein the handle is pivotally coupled to the blade structure and is movable between a deployed position generally perpendicular to the blade structure to a stowed position non-perpendicular to the blade structure.

9. The laryngoscope of claim 8, wherein one of the blade structure and the handle comprises a projection, and the other of the blade structure and the handle comprises an aperture configured and dimensioned to receive the projection in close cooperation and to retain the projection by friction fit, such that engagement locks the handle in a deployed position while allowing the handle to be easily unlatched and returned to the stowed position.

10. The laryngoscope of claim 8, wherein in the stowed position, the handle is parallel to and abutting the blade structure.

11. The laryngoscope of claim 8, wherein the light source comprises a switch including a switch operator externally accessible from the light source, wherein the handle comprises a projection engaging the switch operator when the handle is moved to the deployed position.

12. The laryngoscope of claim 11, wherein the switch operator is flexible, and the projection deforms the flexible switch cover when engaging the switch operator.

13. The laryngoscope of claim 8, wherein the blade structure and the handle are configured to form a continuously curving transition from the blade structure to the handle when the handle is in the deployed position.

14. The laryngoscope of claim 1, further comprising a cushion pad of compliant material permanently affixed to the underside of the straight first blade, to serve as a tooth guard.

15. The laryngoscope of claim 1, further comprising a depth marker visible from the exterior of the laryngoscope when the laryngoscope is inserted into a patient.

* * * * *